United States Patent [19]
Acheson et al.

[11] 3,954,784
[45] May 4, 1976

[54] IMIDAZO[2,1-B]THIAZOLE AND THIAZOLO[3,2-A]-BENZIMIDAZOLE QUATERNARY SALTS AS HYPOGLYCEMIC AGENTS AND GROWTH PROMOTANTS

[75] Inventors: Richard M. Acheson, Oxford; John K. Stubbs, Deal; Charles A. R. Baxter, Sandwich, all of England; Donald E. Kuhla, Gales Ferry, Conn.

[73] Assignee: Pfizer Inc., New York, N.Y.

[22] Filed: Sept. 19, 1974

[21] Appl. No.: 507,384

[30] Foreign Application Priority Data
Sept. 20, 1973 United Kingdom............ 44199/73

[52] U.S. Cl................. 260/306.7 R; 260/240 R; 260/240 D; 260/306.8 R; 260/309.6; 260/309.7; 424/270

[51] Int. Cl.² ....................................... C07D 513/04

[58] Field of Search ............................ 260/306.7 T

[56] References Cited
OTHER PUBLICATIONS
Dorn et al., Chem. Ber., 100, 3246–3259 (1967).

*Primary Examiner*—Raymond V. Rush
*Attorney, Agent, or Firm*—Connolly and Hutz

[57] ABSTRACT

7-Substituted imidazo[2,1-*b*]thiazolium and 9-substitutedthiazolo-[3,2-*a*]benzimidazolium salts as blood-sugar lowering agents and growth promotants.

16 Claims, No Drawings

IMIDAZO[2,1-B]THIAZOLE AND THIAZOLO[3,2-A]-BENZIMIDAZOLE QUATERNARY SALTS AS HYPOGLYCEMIC AGENTS AND GROWTH PROMOTANTS

BACKGROUND OF THE INVENTION

This invention relates to compounds having hypoglycemic and/or growth promotant properties, said compounds being quaternary 7-substituted imidazo [2,1-b]-thiazolium and 9-substituted thiazolo[3,2-a]benzimidazolium salts.

Other than insulin, which is usually administered subcutaneously, the most useful oral medication employed in the treatment of diabetes are the sulfonylureas, many of which are currently being marketed. In addition, biguanides are also employed either alone or in combination with sulfonylureas in the treatment of this disease.

More recently, 1-substituted 3-(2-pyrimidinyl)imidazolium salts have been claimed in Belgium Pat. No. 743,510 and German patent application No. 1,964,282, to be active as hypoglycemic agents. Japanese patent application No. 7305899 reports the synthesis of pyridimium-pyrazine and their use as lowerers of blood sugar and free fatty acid levels. Wiegand, et al., J. Med. Chem., 15, 1326 (1972), review and report on the hypoglycemic activity of a number of azolyl-pyridinium salts.

Most commonly employed growth promotants are members of the anti-bacterial class of quinoxaline-di-N-oxides.

2,3,9-Trimethylbenzimidazo[2,1-b]thiazolium iodide has been prepared by de Stevens, et al., J. Am. Chem. Soc., 79, 5710 (1957), and imidazo[2,1-b]-thiazolium by Kondo, et al., J. Pharm. Soc., Japan, 57, 1050 (1937) (C.A. 32, 3398 (1938) and Kickhofen, et al., Chem. Ber., 88, 1109 (1955) (C.A. 50, 13911 (1956).

SUMMARY OF THE INVENTION

It has now been discovered that quaternary compounds of the formula

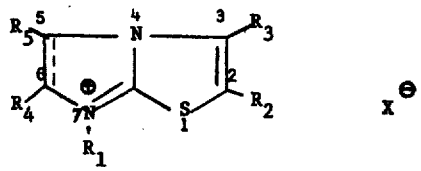

wherein X is a pharmaceutically acceptable anion; $R_1$ is alkyl having from twelve to eighteen carbon atoms, propargyl, allyl, benzyl, phenethyl, styryl, phenylallyl or substituted benzyl wherein said substituent is fluoro, chloro, methoxy, trifluoromethyl, methyl, cyano, phenyl or dichloro; $R_2$ is hydrogen or alkyl having from one to three carbon atoms; $R_3$ is hydrogen, alkyl having from one to three carbon atoms, adamantyl, phenyl or substituted phenyl wherein said substituent is dimethyl or dimethoxy; $R_2$ and $R_3$ when taken together is tetramethylene; $R_4$ is hydrogen, alkyl having one to three carbon atoms, phenyl, dimethylphenyl or chlorophenyl; $R_5$ is hydrogen; and $R_4$ and $R_5$ when taken together with the carbon atoms to which they are attached form a 1,2-phenylene ring are growth promotants and hypoglycemic agents.

The broken line shown in the above structure represents an optional bond such that the present invention is meant to embrace both the 5,6-dihydro and dehydroforms of the imidazo[2,1-b]thiazolium compounds.

A preferred group of hypoglycemic compounds are those wherein $R_1$ is benzyl, $R_2$, $R_4$ and $R_5$ are each hydrogen and $R_3$ is alkyl or adamantyl.

A second preferred group are those wherein $R_1$ is chlorobenzyl, $R_2$, $R_4$ and $R_5$ are each hydrogen and $R_3$ is alkyl containing from 1 to 3 carbon atoms.

A third preferred group included those compounds wherein $R_2$, $R_3$ and $R_5$ are each hydrogen and $R_4$ is phenyl or dimethylphenyl.

A fourth preferred group of hypoglycemic compounds are those wherein $R_1$ is benzyl or substituted benzyl, $R_2$ is hydrogen, $R_3$ is methyl and $R_4$ and $R_5$ taken together with the carbon atoms to which they are attached form a 1,2-phenylene ring.

A fifth preferred class of compounds of the present invention which are growth promotants are those wherein $R_1$ is alkyl having 12 to 18 carbon atoms, $R_2$, $R_4$ and $R_5$ are each hydrogen and $R_3$ is alkyl having one to three carbon atoms.

In all the aforementioned preferred groups of growth promotants and blood sugar lowering agents, it is preferred that X is chloro or bromo.

DETAILED DESCRIPTION OF THE INVENTION

The hypoglycemic agents of the present invention are synthesized by reactions depicted in the following scheme:

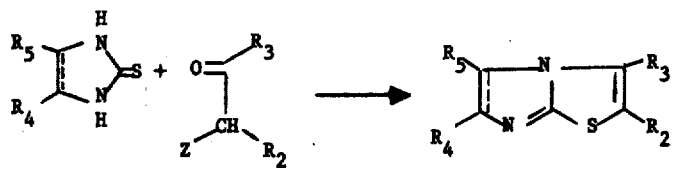

1

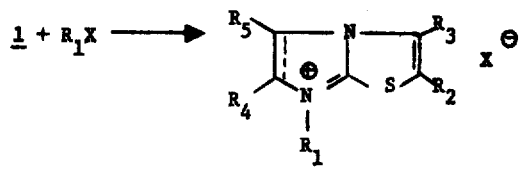

2 wherein X and Z are chloro or bromo and $R_1$, $R_2$, $R_3$, $R_4$ and $R_5$ are as previously indicated.

Experimentally, equimolar amounts of the appropriate 2-mercaptoimidazole or 2-mercapto-4,5-dihydroimidazole and requisite α-halocarbonyl reagent are contacted in a reaction-inert solvent to yield the intermediate compounds 1 as the hydrogen halide salt.

Reaction times and temperatures are not critical. In general, it is preferred that steam bath temperatures be employed in order to hasten the completion of said reaction. Under these conditions the reaction is usually complete in 1–4 hours.

Although the preparation of compounds 1 can be conducted without a solvent, i.e. neat, it is preferred that a solvent be employed. Further, it is preferred that such a solvent be a reaction-inert solvent, i.e. one which will not react with the product or starting reagents to any appreciable extent. Such a solvent should be a non-aqueous, polar solvent and include, for example, lower alkanols, lower alkylnitriles, or dialkyl ketones. The preferred solvent is ethanol.

The reaction product can be isolated from the completed reaction by removal of the solvent or, alternately, by cooling the reaction mixture to induce crystallization of the hydrogen halide salt. When the intermediates 1 have been isolated as the salt they are then converted to the free base by treating an aqueous solution or suspension of said salt with sufficient aqueous sodium hydroxide to liberate the free base, which can be filtered or extracted with a water immiscible solvent.

An alternate method for the preparation of intermediate imidazo[2,1-b]thiazoles is as follows:

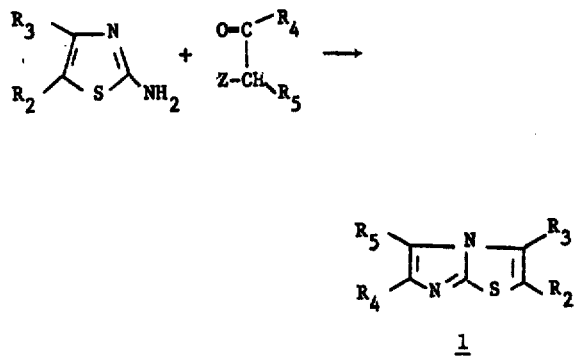

wherein $R_2$, $R_3$, $R_4$, $R_5$ and Z are as previously indicated.

The condensation reaction outlined above is conducted in the same manner as that wherein the starting reagents are a mercaptoimidazole derivative and a halo carbonyl compound. Further, isolation of the product and generation of the free base is effected in the same manner.

Transformation of compounds of formula 1 to quaternary salts of formula 2 is effected by reacting 1 with a halide, $R_1X$, where X is chloro, bromo or iodo. Said reaction can be conducted between equimolar amounts of the two reagents either neat or in the presence of a suitable reaction-inert solvent. When conducted neat a large excess of the halide can be employed, acting under these conditions as both a reactant and solvent.

As previously indicated, by a reaction-inert solvent is meant one which does not react to any appreciable degree with the product or reactants under the conditions of said reaction. Solvents suitable for the solubilizing of the reactants leading to the quaternary compounds 2 can be of a varied nature, and can include (lower)alkanols, (lower)alkylnitriles, di(lower)alkyl ketones, cyclic- and di(lower)alkyl ethers and liquid aromatic hydrocarbons. The preferred solvent for this reaction is acetonitrile.

Reaction time is not critical, and depends on temperature, concentration and inherent reactivity of the reagents. When steam bath temperatures are employed, completion of the reaction usually requires 2 to 4 hours.

The product is isolated by cooling the reaction mixture to induce crystallization, or initial concentration of the reaction mixture followed by cooling. Further purification of the final product is facilitated by trituration or recrystallization from an appropriate solvent.

As mentioned previously, quaternary salt formation is preferably effected with RX wherein X is bromo, chloro or iodo. Following isolation of these salts the nature of the X variable can be altered by initially treating an aqueous solution of quaternary halide with an equivalent of silver oxide, followed by separation of the precipitated silver halide and treatment of the aqueous solution of the quaternary base with at least an equivalent of an appropriate acid HX.

Alternately, the quaternary base can be obtained by passing a solution of a salt through a basic ion-exchange resin column followed by treatment of the eluate with the same or a different acid.

In the utilization of the chemotherapeutic activity of those compounds of the present invention which form quaternary salts, it is preferred, of course, to use pharmaceutically acceptable salts. Although water-insolubility, toxicity, or lack of crystalline nature may make some particular salt species unsuitable or less desirable for use as such in a given pharmaceutical application, the water insoluble or toxic salts can be converted to the corresponding pharmaceutically acceptable quaternary hydroxide by decomposition of the salt as described above, or alternately they can be converted to any desired pharmaceutically acceptable quaternary salt.

Examples of pharmaceutically acceptable anions other than the halides are nitrate, sulfate, phosphate, alkanoates, lactate, citrate, tartrate, succinate and maleate.

Imidazo[2,1-b]thiazole intermediates are prepared by the aforementioned procedures, said procedures being familiar to those skilled in the art and employed in the synthesis of such compounds as reported by Wilson, et al., J. Chem. Soc., 1955, 2943, Fefer, et al., J. Org. Chem, 26, 828 (1961), U.S. Pat. Nos. 2,969,369; 3,267,112 and 3,274,209, Iwai, et al., Chem. Pharm. Bull. -(Tokyo), 12, 813 (1964), Todd, et al., Chem. Ber., 69, 217 (1936), Kondo, et al, J. Pharm. Soc. Japan, 57, 1050 (1937) and Kickhofen, et al., Chem. Ber., 88, 1109 (1955).

The more fundamental starting materials employed in the preparation of the imidazo[2,1-b]thiazoles, i.e., the mercaptoimidazole derivatives, α-halo carbonyl reagents and the 2-aminothiazoles are available either commercially or by synthetic procedures familiar to those skilled in the art.

The imidazo[2,1-b]thiazole and thiazolo[3,2-a]benzimidazole quaternary salts adapted to the therepeutic use as oral hypoglycemic agents are those wherein $R_1$ is propargyl, benzyl, phenethyl or said substituted Benzyl and $R_2$, $R_3$, $R_4$ and $R_5$ are as previously defined. Preferred within this group are 3-methyl-7-benzyl-5,6-dihydroimidazo[2,1-b]thiazolium chloride, 3-methyl-7-benzylimidazo-[2,1-b]thiazolium chloride, 3-methyl-7-(o-chlorobenzyl)imidazo[2,1-b]thiazolium chloride, 3-methyl-7-(p-chlorobenzyl)imidazo[2,1-b]thiazolium chloride, 6-phenyl-7-benzylimidazo[2,1-b]thiazolium chloride, 3-methyl-9-benzylthiazolo-[3,2-a]benzimidazolium bromide, 3-adamantyl-7-benzyl-5,6-dihydroimidazo[2,1-b]thiazolium bromide, 6-(2,4-dimethylphenyl)-7-benzylimidazo[2,1-b]thiazolium bromide, 3-methyl-9-(m-trifluoromethylbenzyl)-thiazolo[3,2-a]benzimidazolium bromide. Those compounds of the present invention which are useful as animal growth promotants are those wherein $R_1$ is alkyl having 12 to 18 carbon atoms, allyl, styryl or phenylallyl and $R_2$, $R_3$, $R_4$ and $R_5$ are as previously defined. Preferred within this group is 3-methyl-7-cetyl-5,6-dihydroimidazo[2,1-b]thiazolium bromide.

The imidazo[2,1-b]thiazolium and thiazolo[3,2-a]benzimidazolium quaternary salts, which are useful hypoglycemic agents in mammals, can be administered either as individual therapeutic agents or as mixtures of therepeutic agents. They can be administered alone, but are generally administered with a pharmaceutical carrier selected on the basis of the chosen route of administration and standard pharmaceutical practice. For example, they may be combined with various pharmaceutically acceptable carriers in the form of tablets, capsules, lozenges, troches, hard candies, powders, aqueous suspensions or solutions, injectable solutions, elixirs, syrups and the like. Such carriers include solid diluents or filters, sterile aqueous media and various nontoxic organic solvents. Moreover, the oral pharmaceutical compositions of this invention may be suitably sweetened and flavored by means of various agents of the type commonly used for this purpose.

The particular carrier selected and the proportion of active ingredient to carrier are influenced by the solubility and chemical nature of the therapeutic compounds, the chosen route of administration and the needs of the standard pharmaceutical practice. For example, where those compounds are administered orally in tablet form, excipients such as lactose, sodium citrate, calcium carbonate and dicalcium phosphate may be used. Various disintegrants such as starch, alginic acids, and certain complex silicates, together with lubricating agents such as magnesium stearate, sodium lauryl sulphate and talc, may also be used in producing tablets for the oral administration of these compounds. For oral administration in capsule form, high molecular weight polyethylene glycols are among the preferred materials for use as pharmaceutically acceptable carriers. Where aqueous suspensions are to be used for oral administration, the compounds of this invention may be combined with emulsifying or suspending agents. Diluents such as ethanol, propylene glycol, glycerine and their combinations may be employed as well as other materials.

For purposes of parenteral administration, solutions or suspensions of the instant compounds in sesame or peanut oil or in aqueous propylene glycol solutions can be employed, as well as sterile aqueous solutions described hereinafter. These particular solutions are especially suited for intramuscular and subcutaneous injection purposes. The aqueous solutions dissolved in pure distilled water are also useful for intravenous injection purposes provided that their pH is properly adjusted beforehand. Such solutions should also be suitably buffered, if necessary, and the liquid diluent first rendered isotonic with sufficient saline.

It is necessary that the active ingredient form a proportion of the composition such that a suitable dosage form will be obtained. Obviously, several dosage unit forms may be administered at about the same time. Although compositions with less than 0.005 percent by weight of active ingredient might be used in certain instances, it is preferred to use compositions containing not less than 0.005 percent of the active ingredient; otherwise the amount of carrier becomes excessively large. Activity increases with the concentration of the active ingredient. The composition may contain 10, 50, 75, 95, or an even higher percentage by weight of the active ingredient.

Although the use of the present invention is directed toward the treatment of mammals in general, the preferred subject is humans. In determining an efficacious dose for human therapy, results of animal testing are frequently extrapolated and a correlation is assumed between animal test behavior and proposed human dosage. When a commercially employed standard is available, the dose level of the clinical candidate in humans is frequently determined by comparison of its performance with the standard in an animal test. For example, β-phenethylbiguanide is employed as a standard hypoglycemic agent and is administered to humans at the rate of 50 to 150 mg. daily. It is assumed, then, that if compounds of the present invention have activity comparable to β-phenethylbiguanide in the test assay, that similar doses will provide comparable responses in humans.

Obviously, the physician will ultimately determine the dosage which will be most suitable for a particular individual, and it will vary with the age, weight and response of the particular patient as well as with the nature and extent of the symptoms and the pharmacodynamic characteristics of the particular agent to be administered. Generally, small doses will be administered initially, with a gradual increase in the dosage until the optimum level is determined. It will often be found that when the composition is administered orally, larger quantities of the active ingredient will be required to produce the same level as produced by a small quantity administered parenterally.

Having full regard for the foregoing factors, it is considered that an effective daily dosage of the compounds of the present invention in humans of approximately 50 to 600 mg. per day, with a preferred range of about 50 to 400 mg. per day in single or divided doses, or at about 0.07 to 0.6 mg./kg. of body weight will effectively lower blood sugar levels in human diabetic subjects. These values are illustrative, and there may, of course, be individual cases where higher or lower dose ranges are merited.

For use as a growth promotant or agent for improving feed conversion efficiency in animals, the compounds of the invention will generally be administered in the animal feed or drink. For convenience of distribution, a compound will normally be marketed in the form of a concentrate in which the compound is mixed with an inert diluent such as limestone or oystershell powder or with other feed components. It is expected that the compounds of the invention would be used at a level of from 1 to 500 g. per ton of feed or 1 to 500 mg. per liter of drinking water, or at correspondingly higher levels in concentrates for subsequent mixture with the feed or drinking water.

Thus the present invention yet further provides an animal food or drink, or a concentrate for addition thereto, containing one or more of the previously described compounds, and also a method of improving

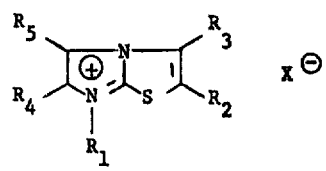

| R₁ | R₂ | R₃ | R₄ | R₅ | X | m.p.,°C. |
|---|---|---|---|---|---|---|
| C₆H₅CH₂— | H— | H— | H— | H— | Br | 147–149 |
| C₆H₅CH₂— | H— | CH₃— | H— | H— | Br | 138 |
| C₆H₅CH₂— | H— | C₆H₅— | H— | H— | Br | 185–186 |
| C₆H₅CH₂— | CH₃— | CH₃— | H— | H— | Br | 140 |
| C₆H₅CH₂— | —(CH₂)₄— |  | H— | H— | Br | 177 |
| 2-ClC₆H₄CH₂— | H— | CH₃— | H— | H— | Br | 221–223 |
| 3-ClC₆H₄CH₂— | H— | CH₃— | H— | H— | Br | 177–180 |
| 4-ClC₆H₄CH₂— | H— | CH₃— | H— | H— | Cl | 205–208 |
| 2,4-Cl₂C₆H₃CH₂— | H | CH₃— | H— | H— | Cl | 272–275 |
| 2,6-Cl₂C₆H₃CH₂— | H— | CH₃— | H— | H— | Br | 243–245 |
| 3-FC₆H₄CH₂— | H— | CH₃— | H— | H— | Br | 170–171 |
| 4-FC₆H₄CH₂— | H— | CH₃— | H— | H— | Br | 218–219 |
| 3-CF₃C₆H₄CH₂— | H— | CH₃— | H— | H— | Br | 168–170 |
| 4-CH₃OC₆H₄CH₂— | H— | CH₃— | H— | H— | Br | 191–192 |
| 4-C₆H₅C₆H₄CH₂— | H— | CH₃— | H— | H— | Br | 186–187 |
| C₆H₅CH₂CH₂— | H— | CH₃— | H— | H— | Br | 117–120 |
| CH≡CCH₂— | —(CH₂)₄— |  | H— | H— | Br | 196–198 |
| C₆H₅CH₂— | H— | 2,5-(CH₃O)₂C₆H₃— | H— | H— | Br | 161–163 |
| C₆H₅CH₂— | H— | 2,4-(CH₃)₂C₆H₃— | H— | H— | Br | 203–205 |
| C₆H₅CH₂— | CH₃— | C₆H₅— | H— | H— | Br | 210–213 |
| C₆H₅CH₂— | H— | -⟨⟩ (cyclohexyl) | H— | H— | Br | 182–185 |
| CH₃(CH₂)₁₄CH₂— | H | CH₃ | H— | H | Br | 108–110 |
| 4-NCC₆H₄CH₂— | H— | CH₃ | H— | H | Br | 212 |
| 2-CH₃C₆H₄CH₂— | H— | CH₃ | H— | H | Br | 201–204 |
| C₆H₅CH=CHCH₂ | H— | CH₃ | H— | H | Cl | 150–151 |
| CH₂=CHCH₂ | H— | CH₃ | H— | H | Br | 89–90 |
| CH₃(CH₂)₁₄CH₂ | H— | C₆H₅ | H— | H— | Br | 169–170 | the growth, feed conversion efficiency of an animal which comprises administering to the animal an effective amount of one or more of the growth promotant compounds previously described.

The following examples are provided solely for the purpose of illustration and are not to be construed as limitations of this invention, many variations of which are possible without departing from the spirit or scope thereof.

EXAMPLE 1

7-Propargyl-3-methyl-5,6-dihydroimidazo[2,1-b]thiazolium bromide (R₁ =CH≡CCH₂; R₂ = H; R₃ = CH₃; R₄ and R₅ = H; X = Br)

A solution of 12 g. of propargyl bromide and 14 g. of 3-methyl-5,6-dihydroimidazo[2,1-b]thiazole (prepared by basification of 3-methyl-5,6-di-hydroimidazo[2,1-b]thiazole hydrochloride with 5N sodium hydroxide solution) in 160 ml. of dry acetonitrile is allowed to stir at room temperature for 16 hrs. The solution is concentrated to a small volume and the precipitated product filtered. The purified product is obtained by recrystallization from acetonitrile-ethyl acetate, 21 g., m.p. 207°–208° C.

Anal. Calc'd for C₉H₁₁BrN₂S: N, 10.8; Br: 30.9. Found: N, 10.5; Br: 31.2.

EXAMPLE 2

Employing the procedure of Example 1, and starting with the requisite reagents, heating them under reflux for 16 hours, the following 5,6-dihydrocongeners are synthesized:

EXAMPLE 3

The procedure of Example 1 is again repeated, starting with the appropriate 5,6-dihydroimidazo[2,1-b]thiazole and halide (R₁X) to provide the following compounds:

2-ethyl-3,6-dimethyl-7-(p-trifluoromethylbenzyl)-5,6-dihydroimidazo[2,1-b]thiazolium chloride, 2-i-propyl-6-phenyl-7-(p-trifluoromethylbenzyl)-5,6-dihydroimidazo[2,1-b]thiazolium chloride, 2-methyl-3-(2,4-dimethylphenyl)-7-(p-phenylbenzyl)-5,6-dihydroimidazo[2,1-b]thiazolium bromide, 3-(3,5-dimethylphenyl)-6-ethyl-7-(omethoxybenzyl)-5,6-dihydroimidazo[2,1-b]thiazolium bromide, 2,3-di-n-propyl-6-(m-chlorophenyl)-7-(p-chlorobenzyl)-5,6-dihydroimidazo[2,1-b]thiazolium chloride, 3-adamantyl-6-phenyl-7-(o-fluorobenzyl)-5,6-dihydroimidazo[2,1-b]thiazolium chloride, 3-(2,4-dimethylphenyl-6-(3,5-dimethylphenyl)-7-benzyl-5,6-dihydroimidazo[2,1-b]thiazolium chloride, 2-methyl-3-(3,5-dimethoxyphenyl)-6-(p-chlorophenyl)-7-(m-trifluoromethylbenzyl)-5,6-dihydroimidazo[2,1-b]thiazolium bromide, 3-adamantyl-7-propargyl-5,6-dihydroimidazo[2,1-b]thiazolium bromide, 2,3,6-triethyl-7-(p-chlorobenzyl)-5,6-dihydroimidazo[2,1-b]thiazolium chloride, 1-(m-trifluoromethylbenzyl)-2,3-dimethyl-2,3,5,6,7,8-hexahydroimidazo[2,1-b]benzthiazolium chloride and 1-benzyl-2-phenyl-2,3,5,6,7,8-hexahydroimidazo[2,1-b]benzthiazolium bromide.

EXAMPLE 4

3-Methyl-7-benzylimidazo[2,1-b]thiazolium bromide ($R_1 = C_6H_5CH_2$; $R_2 = H$; $R_3 = CH_3$; $R_4$ and $R_5 = H$; $X = Br$)

Nineteen grams of 3-methylimidazo[2,1-b]thiazole, obtained by treating 23.2 g. of the hydrochloride salt in 300 ml. of water with sufficient 20% sodium hydroxide solution to render it strongly basic, is dissolved in 250 ml. of acetonitrile and subsequently treated with 27.4 g. of benzyl bromide. The reaction mixture is heated under reflux for 2 hrs., and it is then cooled and treated with 150 ml. of diethyl ether. The product is filtered and recrystallized from acetonitrile-ethyl acetate, 37.4 g., m.p. 165°–167.5° C.

Anal. Calc'd for $C_{13}H_{13}BrN_2S$: C, 50.5; H, 4.2; N, 9.1. Found: C, 50.2; H, 4.3; N, 9.2.

EXAMPLE 5

Starting with the appropriate imidazo[2,1-b]thiazole and requisite halide, and repeating the procedure of Example 4, the following quaternary salts are prepared:

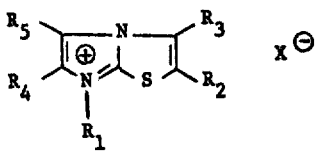

| $R_1$ | $R_2$ | $R_3$ | $R_4$ | $R_5$ | X | m.p.,°C. |
|---|---|---|---|---|---|---|
| $C_6H_5CH_2$— | H— | H— | $CH_3$— | H— | Br | 220 |
| $C_6H_5CH_2$— | H— | H— | $C_6H_5$— | H— | Br | 176–178 |
| $C_6H_5CH_2$— | H— | H— | p-$ClC_6H_4$— | H— | Br | 195–197 |
| o-$ClC_6H_4CH_2$— | H— | $CH_3$— | H— | H— | Cl | 174–177 |
| m-$ClC_6H_4CH_2$— | H— | $CH_3$— | H— | H— | Cl | 156–159 |
| 2,6-$Cl_2C_6H_3CH_2$— | H— | $CH_3$— | H— | H— | Cl | 225–229 |
| 2,4-$Cl_2C_6H_3CH_2$— | H— | $CH_3$— | H— | H— | Cl | 269–271 |
| p-$ClC_6H_4CH_2$— | H— | $CH_3$— | H— | H— | Cl | 206–209 |
| p-$CH_3OC_6H_4CH_2$— | H— | $CH_3$— | H— | H— | Cl | 136–139 |
| $C_6H_5CH_2$— | H— | $CH_3$— | H— | H— | Cl | 152–155 |
| $C_6H_5CH_2CH_2$— | H— | $CH_3$— | H— | H— | Br | 206–209 |
| $C_6H_5CH_2$— | H— | H— | 2,4-$(CH_3)_2C_6H_3$— | H— | Br | 170–172 |

EXAMPLE 6

The procedure of Example 4 is again repeated, starting with the requisite reagents, to provide the following imidazo[2,1-b]thiazolium salts:

2-methyl-3,4-diethyl-7-benzylimidazo[2,1-b]thiazolium chloride; 2-n-propyl-3,4-diethyl-7-(p-fluorobenzyl)imidazo[2,1-b]thiazolium chloride, 2-i-propyl-7-(p-fluorobenzyl)imidazo[2,1b]thiazolium chloride; 3-phenyl-7-(o-methoxybenzyl)imidazo[2,1-b]thiazolium bromide; 3-adamantyl-6-phenyl-7-(m-trifluorobenzyl)imidazo[2,1-b]thiazolium bromide; 3-(3,5-dimethoxybenzyl)-7-benzylimidazo[2,1-b]thiazolium chloride, 3-methyl-7-(p-phenylbenzyl)imidazo[2,1-b]thiazolium bromide; 3-(2,4-dimethylbenzyl)-6-methyl-7-(p-chlorobenzyl)imidazo[2,1-b]thiazolium bromide; 3-(p-chlorophenyl)-7-propargylimidazo[2,1-b]thiazolium bromide; 3,6-bis(2,4-dimethylphenyl)-7-benzylimidazo[2,1-b]thiazolium chloride; 1-(p-fluorobenzyl-5,6,7,8-tetrahydroimidazo[2,1-b]benzthiazolium chloride and 1-propargyl-5,6,7,8-tetrahydroimidazo[2,1-b]benzthiazolium bromide.

EXAMPLE 7

3-Methyl-9-benzylthiazolo[3,2-a]benzimidazolium bromide ($R_1 = C_6H_5CH_2$; $R_2 = H$; $R_3 = CH_3$; $R_4$ and $R_5 = -CH=CH-CH=CH-$; $X = Br$)

Starting with 3-methylthiazolo[3,2-a]benzimidazole and benzyl bromide and repeating the procedure of Example 1, the desired product is obtained, m.p. 227°–229° C.

EXAMPLE 8

The procedure of Example 1 is repeated wherein the appropriate thiazolo[3,2-a]benzimidazole is condensed with the requisite halide to provide the following quaternary salts:

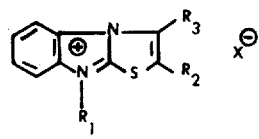

| $R_1$ | $R_2$ | $R_3$ | X |
|---|---|---|---|
| $C_6H_5CH_2$— | $CH_3$— | H— | Cl |
| m-$ClC_6H_4CH_2$— | $CH_3$— | $CH_3$— | Br |
| p-$ClC_6H_4CH_2$— | $CH_3$— | $CH_3$— | Cl |
| p-$FC_6H_4CH_2$— | H— | $C_6H_5$— | Cl |
| m-$CH_3OC_6H_4CH_2$— | H— | $C_6H_5$— | Cl |
| m-$CH_3OC_6H_4CH_2$— | $CH_3$— | $C_6H_5$— | Cl |
| m-$CF_3C_6H_4CH_2$— | H— | 2,4-$(CH_3)_2C_6H_3$— | Cl |
| CH≡C—$CH_2$— | H— | 2,4-$(CH_3)_2C_6H_3$— | Br |

| | | | |
|---|---|---|---|
| CH≡C—$CH_2$— | H— | $C_6H_5$— | Br |
| p-$C_6H_5C_6H_4CH_2$ — | H— | (cyclohexyl) | Br |
| 2,4-$Cl_2C_6H_3CH_2$— | H— | 2,4-$(CH_3O)_2C_6H_3$— | Cl |
| 2,6-$Cl_2C_6H_3CH_2$— | H— | 2,4-$(CH_3O)_2C_6H_3$— | Cl |
| 3,5-$Cl_2C_6H_3CH_2$— | H— | $C_2H_5$— | Cl |
| m-$CH_3OC_6H_4CH_2$— | $C_2H_5$— | $C_2H_5$— | Br |

EXAMPLE 9

The procedure of Example 1 is again repeated, wherein the requisite thiazolo[3,2-a]benzimidazole is condensed with the appropriate halide to provide the following quaternary salts:

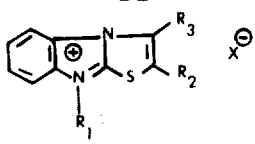

| $R_1$ | $R_2$ | $R_3$ | X | m.p.,°C. |
|---|---|---|---|---|
| $C_6H_5CH_2-$ | H | $CH_3-$ | Br | 229–231 |
| $n\text{-}C_{10}H_{33}-$ | H | $CH_3-$ | Br | 160–1 |
| $C_2H_5-$ | H | $CH_3-$ | Br | 284 |
| Cl-C₆H₄-CH₂- | H | $CH_3-$ | Cl | 227–9 |
| C₆H₅-(CH₂)₂- | H | $CH_3-$ | Br | 197–8 |
| CF₃-C₆H₄-CH₂- | H | $CH_3-$ | Cl | 234 |
| $CH_2=CH.CH_2-$ | H | $CH_3$ | Br | 256–7 |
| F-C₆H₄-CH₂- | H | $CH_3-$ | Cl | 223–5 |
| Cl,Cl-C₆H₃-CH₂- | H | $CH_3-$ | Cl | 233–6 |
| NC-C₆H₄-CH₂- | H | $CH_3-$ | Br | 314–5 |
| Cl-C₆H₄-CH₂- | H | $CH_3-$ | Br | 234–4 |
| CH₃-C₆H₄-CH₂- | H | $CH_3-$ | Cl | 218–9 |
| NC-C₆H₄-CH₂- | H | $CH_3-$ | Br | 252 |

EXAMPLE 10

3-Methyl-7-benzylimidazo[2,1-b]thiazolium Chloride

A. A solution of 3.09 g. of 3-methyl-7-benzylimidazo[2,1-b]thiazolium bromide in 35 ml. of water is treated with 1.15 g. of silver oxide and the mixture allowed to stir at room temperature for several hours. The reaction mixture is centrifuged and the supernatant decanted from the silver bromide. Aqueous hydrochloric acid (11 ml. of a 1 M solution) is added to the clear supernatant and the water removed in vacuo. The residual quaternary salt is triturated with diethyl ether and subsequently filtered and recrystallized from acetonitrile-ethyl acetate.

In a similar manner the quaternary bromide salts in Examples 1 through 8 are converted to the quaternary chloride salts.

B. The procedure of Example 10A is repeated, 1.8 ml. of 6N nitric acid being substituted for the 11 ml. of 1N hydrochloric acid, to provide 3-methyl-7-benzylimidazo[2,1-b]thiazolium nitrate.

EXAMPLE 11

In a manner similar to that in Example 10, the quaternary chloride and bromide salts prepared in Examples 1 through 9 are converted to other quaternary salts wherein the anion of the resulting salt, X, is a pharmaceutically acceptable anion.

EXAMPLE 12

Hypoglycemic Testing

The hypoglycemic testing of the compounds of the present invention is carried out by a standard procedure, and comprises grouping eight, Hartley strain, male guinea pigs which have been fasted 18–24 hrs. in each group. Blood samples are obtained from the pentobarbital-anesthetized animals by cardiac puncture. Each of the eight animals is dosed i.p. with a given dose of the test compound. Blood samples are taken at 1, 2 and 4 hours following the dosing, and the venous blood diluted 1:10 with saltine and assayed for blood sugar levels on an Auto-Analyzer, the levels being expressed as mg.%. The activity for the test compound is expressed as the percent lowering of the blood sugar at the 1, 2 and 4 hr. when compared with the blood sugar level of a group of eight control animals which have been similarly dosed with a saline solution.

Each of the following representative imidazo[2,1-b]thiazolium salts was tested as hypoglycemic agent following the above mentioned procedure, and was found to be active at the indicated dose level.

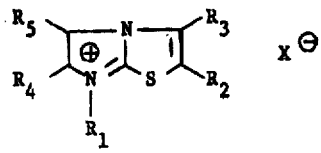

| | | | | | | | % Fall Blood Sugar Level | | |
|---|---|---|---|---|---|---|---|---|---|
| $R_1$ | $R_2$ | $R_3$ | $R_4$ | $R_5$ | X | Dose, mg./kg. | $T_1$ | $T_2$ | $T_4$ |
| $C_6H_5CH_2-$ | H— | $CH_3-$ | H— | H— | Br | 50 | 36 | 82 | 88 |
| $C_6H_5CH_2CH_2-$ | H— | $CH_3-$ | H— | H— | Br | 50 | 12 | 17 | — |
| m-ClC₆H₄CH₂— | H— | $CH_3-$ | H— | H— | Br | 50 | 18 | 45 | 79 |
| p-C₆H₅C₆H₄CH₂— | H— | $CH_3-$ | H— | H— | Br | 100 | 43 | 60 | — |
| $C_6H_5CH_2-$ | H— | $C_6H_5-$ | H— | H— | Br | 100 | 30 | 29 | 22 |

-continued

| R₁ | R₂ | R₃ | R₄ | R₅ | X | Dose, mg./kg. | T₁ | T₂ | T₄ |
|---|---|---|---|---|---|---|---|---|---|
| CH≡CCH₂— | H— | CH₃— | H— | H— | Br | 50 | — | 18 | 20 |
| C₆H₅CH₂— | —(CH₂)₄— | | H— | H— | Br | 50 | 45 | 87 | — |
| p-ClC₆H₄CH₂— | H— | CH₃— | H— | H— | Cl | 50 | 8 | 18 | 42 |
| 2,4-Cl₂C₆H₃CH₂— | H— | CH₃— | H— | H— | Cl | 50 | 20 | 48 | — |
| p-FC₆H₄CH₂— | H— | CH₃— | H— | H— | Cl | 50 | 16 | 38 | 77 |
| C₆H₅CH₂— | CH₃ | CH₃— | H— | H— | Br | 50 | 14 | 45 | 62 |
| C₆H₅CH₂— | H— | H— | H— | H— | Br | 50 | 40 | 76 | 86 |
| m-CF₃C₆H₄CH₂— | H— | CH₃— | H— | H— | Cl | 50 | — | 10 | 12 |
| C₆H₅CH₂— | H | 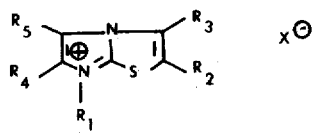 | H— | H— | Br | 50 | 11 | 15 | 32 | and

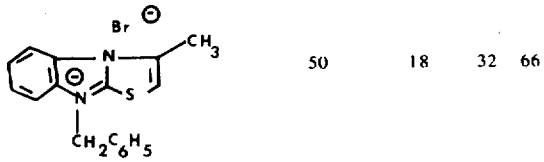

| R₁ | R₂ | R₃ | R₄ | R₅ | X | Dose, mg./kg. | T₁ | T₂ | T₄ |
|---|---|---|---|---|---|---|---|---|---|
| C₆H₅CH₂— | H— | H— | CH₃— | H— | Br | 50 | 29 | 68 | 79 |
| C₆H₅CH₂— | H— | CH₃— | H— | H— | Br | 25 | 20 | 62 | 66 |
| p-CH₃OC₆H₄CH₂— | H— | CH₃— | H— | H— | Cl | 100 | 33 | 83 | — |
| p-ClC₆H₄CH₂— | H— | CH₃— | H— | H— | Cl | 25 | 11 | 16 | 39 |
| 2,4-Cl₂C₆H₃CH₂— | H— | CH₃— | H— | H— | Cl | 50 | 8 | 65 | — |
| C₆H₅CH₂— | H— | H— | C₆H₅—H— | | Br | 25 | 6 | 26 | 84 |
| C₆H₅CH₂— | H— | H— | p-ClC₆H₄— | H— | Br | 50 | 5 | 35 | 78 |
| C₆H₅CH₂CH₂— | H— | CH₃— | H— | H— | Br | 50 | 26 | 70 | 85 | and

[structure of benzylimidazothiazolium bromide with CH₃ and CH₂C₆H₅ substituents]    50    18    32    66

EXAMPLE 13

3-Methyl-7-benzylimidazo[2,1-b]thiazolium chloride

A column 1 inch × 20 inches is packed with Amberlite IRA-400 which has been slurried in 2N sodium hydroxide solution. After the column material is washed with deionized water, a solution of 5.0 g. of 3-methyl-7-benzylimidazo[2,1-b]thiazolium bromide in 50 ml. of water is applied. The water eluates are collected until the pH of said eluates is neutral. The combined eluates are treated with 200 ml. of 6N hydrochloric acid and concentrated to dryness. The crystallized product is further purified by recrystallization from acetonitrile-ethyl acetate, 1.22 g., m.p. 152°–155° C.

In a similar manner the quaternary salts of Exaples 1 through 8 are converted to other quaternary salts wherein the resulting salt anion, X, is a pharmaceutically acceptable one.

EXAMPLE 14

3-methyl-7-Styryl-5,6-dihydro-imidazo[2,1-b]thiazolium chloride a. The compound 3-methyl-7-phenacyl-5,6-dihydro-imidazo[2,1-b]thiazolium chloride is prepared by the method of Example 1, using phenacyl chloride instead of propargyl bromide. This compound has a m.p. 162°–4°C. and is used in the next stage.

b. The product of (a) (23.4 g.) is dissolved in water (60 ml.) and stirred at room temperature while sodium borohydride (0.8 g.) is added in portions. After 5–10 min. the solution is acidified with conc. hydrochloric acid and evaporated to dryness, using dioxan to remove the last of the water by azeotropy. The residue is extracted with boiling acetonitrile (150 ml.), filtered, and hot ethyl acetate (100 ml.) is added to the hot filtrate. On cooling, the N-(2-hydroxy-2-phenylethyl compound crystallizes 12.7 g., as colourless plates and is recrystallized from acetonitrile-ethyl acetate, m.p. 195°.

c. The product of (b) (12.5 g.) dissolved in benzoyl chloride (40 ml.) is stirred and heated on a silicone oil bath at 200° for 1 hr., then cooled. After standing at 0° overnight the solid is filtered off, washed with acetone and then ether, and recrystallized from acetonitrile (with a little methanol added) to give the desired styryl product (5.5 g.), as pale yellow platelets, m.p. 280° (decomp.).

Anal. Calc'd for $C_{14}H_{15}ClN_2S$: Cl, 12.7; N, 10.0. Found: C, 12.4; N, 9.9.

What is claimed is:

1. A compound of the formula

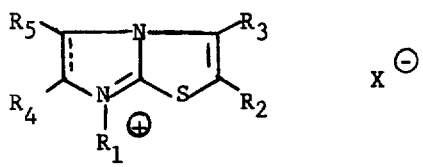

wherein

X is a pharmaceutically acceptable anion;

$R_1$ is selected from the group consisting of propargyl, benzyl, phenethyl, and substituted benzyl wherein said substituent is selected from the group consisting of fluoro, chloro, methoxy, trifluoromethyl, methyl, cyano, phenyl and dichloro;

$R_2$ is selected from the group consisting of hydrogen and alkyl having from one to three carbon atoms;

$R_3$ is selected from the group consisting of hydrogen, alkyl having from one to three carbon atoms, adamantyl, phenyl and substituted phenyl wherein said substituent is selected from the group consisting of dimethyl and dimethoxy;

$R_2$ and $R_3$ when taken together is tetramethylene;

$R_4$ is selected from the group consisting of hydrogen, alkyl having from one to three carbon atoms, phenyl, dimethylphenyl and chlorophenyl;

$R_5$ is hydrogen and $R_4$ and $R_5$ when taken together with the carbon atoms to which they are attached form an 0-phenylene ring.

2. A compound of claim 1 wherein X is chloro, $R_1$ is benzyl, $R_2$, $R_4$ and $R_5$ are each hydrogen and $R_3$ is alkyl having from one to three carbon atoms.

3. The compound of claim 2, 3-methyl-7-benzyl-5,6-dihydroimidazo[2,1-b]thiazolium chloride.

4. The compound of claim 2, 3-methyl-7-benzylimidazo[2,1-b]thiazolium chloride.

5. A compound of claim 1 wherein X is chloro, $R_1$ is chlorobenzyl, $R_2$ $R_4$ and $R_5$ are each hydrogen and $R_3$ is alkyl having from one to three carbon atoms.

6. The compound of claim 5, 3-methyl-7-(o-chlorobenzyl)imidazo[2,1-b]thiazolium chloride.

7. The compound of claim 5, 3-methyl-7-(p-chlorobenzyl)imidazo[2,1-b]thiazolium chloride.

8. A compound of claim 1 wherein X is chloro, $R_2$, $R_3$ and $R_5$ are each hydrogen and $R_4$ is selected from the group consisting of phenyl and dimethylphenyl.

9. The compound of claim 8, 6-phenyl-7-benzylimidazo[2,1-b]thiazolium chloride.

10. The compound of claim 8, 6-(2,4-dimethylphenyl)-7-benzylimidazo[2,1-b]thiazolium chloride.

11. A compound of claim 1 wherein $R_1$ is selected from the group consisting of benzyl and said substituted benzyl, $R_2$ is hydrogen, $R_3$ is methyl and $R_4$ and $R_5$ taken together with the carbon atoms to which they are attached form an o-phenylene ring.

12. The compound of claim 11, 3-methyl-9-benzylthiazolo[3,2-a]benzimidazolium bromide.

13. The compound of claim 11, 3-methyl-9-(m-trifluoromethylbenzyl)thiazolo[3,2a]benzimidazolium chloride.

14. The compound of claim 11, 3-methyl-9-(p-cyanobenzyl)thiazolo [3,2-a]benzimidazolium bromide.

15. A compound of claim 1 wherein X is bromo, $R_1$ is benzyl and $R_2$, $R_4$ and $R_5$ are each hydrogen.

16. The compound of claim 15, 3-adamantyl-7-benzyl-5,6-dihydroimidazo[2,1-b]thiazolium bromide.

* * * * *